United States Patent [19]

Eggers

[11] Patent Number: 5,208,022

[45] Date of Patent: May 4, 1993

[54] NON-MALIGNANT CELLS COUPLED TO ADJUVANTS AND THEIR USE IN A METHOD TO INDUCE ANTI-TUMOR IMMUNITY

[75] Inventor: Arnold E. Eggers, New York, N.Y.

[73] Assignee: State University of New York (Suny), Albany, N.Y.

[21] Appl. No.: 627,555

[22] Filed: Dec. 10, 1990

Related U.S. Application Data

[63] Continuation of Ser. No. 196,037, May 19, 1988, abandoned.

[51] Int. Cl.$^5$ .................. A61K 39/00; A61K 37/02
[52] U.S. Cl. .......................... 424/88; 424/89; 424/90; 424/91; 424/92; 424/93; 530/402; 530/403; 530/404; 530/405; 530/406; 512/2; 435/240.1
[58] Field of Search .............. 424/88, 95, 89, 90, 424/91, 92, 93; 530/402, 403, 404, 405, 406; 514/2; 435/240.1

[56] References Cited

U.S. PATENT DOCUMENTS 4,186,194  1/1980  Adam et al. ...................... 424/89

OTHER PUBLICATIONS

Lederer et al., *Chemistry and Physics of Lipids*, vol. 16, pp. 91-106, 1976.
Toubiana et al, *Cancer Immunol. Immunother*, vol. 2, pp. 189-193, 1977.
Yorkoni et al, *J. Natl. Cancer Inst.* vol. 51, pp. 717-720, 1973.
Kotani et al, *Federation Proc.* vol. 45, pp. 2534-2540, 1986.
Adam et al, *Molec. Cell. Biochem*, vol. 41, pp. 27-47, 1981.
Eggers et al, Cancer Immunol. Immunother. vol. 19, pp. 43-45, 1985.
Glimcher et al, Journal Experimental Medicine, vol. 154, pp. 1652-1670, Nov. 1981.
Eggers et al., Journal of Biological Response Modifiers, vol. 3, pp. 387-390, 1984.
Schinder et al, Int. J. Immunopharamac. vol. 8, No. 5, pp. 487-498, 1986.

*Primary Examiner*—Michael G. Wityshyn
*Assistant Examiner*—Abdel A. Mohamed
*Attorney, Agent, or Firm*—Morgan & Finnegan

[57] ABSTRACT

A vaccine composition for inducing anti-tumor immunity comprising non-malignant cells, preferably syngeneic non-malignant cells, coupled with adjuvant compounds. The nonmalignant immunizing cells of the present invention induce T-cell mediated cytoxicity which cross-reacts with tumor cells, providing in vivo protection against the tumor cells. Examples of turmors which may be treated by administration of the vaccine compositions include fibrosarcomas, glioblastomas, and all solid and lymphoid tumors.

26 Claims, No Drawings

NON-MALIGNANT CELLS COUPLED TO ADJUVANTS AND THEIR USE IN A METHOD TO INDUCE ANTI-TUMOR IMMUNITY

This is a continuation of copending application Ser. No. 07/196,037, filed on May 19, 1988, now abandoned.

FIELD OF THE INVENTION

The present invention relates to a novel vaccine composition for inducing anti-tumor immunity, more particularly the present invention relates to a novel vaccine composition comprising non-malignant cells coupled to adjuvant compounds and its use in a method for inducing anti-tumor immunity.

BACKGROUND OF THE INVENTION

The human body posses the ability to resist most types of organisms, microorganisms or toxins that can cause damage to tissues and organs. This capacity is referred to as immunity. Much of the immunity is caused by an immunity system that forms antibodies and/or sensitized lymphocytes that attack and destroy the organisms, microorganisms or toxins.

This type of immunity is commonly referred to as acquired immunity.

However, an additional portion of the immunity results from general processes rather than from processes directed at specific disease organisms. This is called innate immunity. Examples of innate immunity include Phagocytosis of bacteria and other invaders by white blood cells and reticuloendothelial cells; destruction of organisms swallowed into the stomach by the acid secretions of the stomach and by the digestive enzymes; resistance of the skin to invasion by organisms; and presence in the blood of special chemical compounds that attach to foreign organisms or toxins and destroy them.

In addition to its innate immunity, the human body also has the ability to develop extremely powerful specific immunity against individual invading agents such as lethal bacteria, viruses, toxins, and foreign tissues from other animals. This is called acquired immunity or adaptive immunity.

This system of acquired immunity is important as a Protection against invading organisms to which the body does not have innate immunity. The body does not block the invasion upon first exposure to the invader. However, within a few days to a few weeks after exposure, the special immune system develops extremely powerful resistance to the invader. Furthermore, the resistance is highly specific for that Particular invader and not for others.

Acquired immunity can often bestow significant and long term protection. This is the reason the process known as vaccination is so important in the protection against disease.

Two basic, but related types of acquired immunity occur in the body. In one of these the body develops circulating antibodies, which are globulin molecules that are capable of attacking the invading agent. This type of immunity is called humoral immunity. The second type of immunity is achieved through the formation of large numbers of highly specialized lymphocytes that are specifically sensitized against the foreign agent. These sensitized lymphocytes have the special capability to attach to the foreign agent and to destroy it. This type of immunity is called cellular or cell-mediated immunity or, sometimes, lymphocytic immunity.

Both the antibodies and the sensitized lymphocytes are formed in the lymphoid tissue of the body. The presence of antigens initiate the immune process.

Acquired immunity is the product of the body's lymphoid tissue. The lymphoid tissue is located mostly in the lymph nodes, but it is also found in special lymphoid tissue such as that of the spleen, in submucosal areas of the gastrointestinal tract, and, to a slight extent, in the bone marrow. The lymphoid tissue is distributed advantageously in the body to intercept the invading organisms or toxins before they can spread too widely.

Though most of the lymphocytes in normal lymphoid tissue look alike when studied under the microscope, these cells are distinctly divided into two separate populations. One of the populations is responsible for forming the sensitized lymphocytes that provide cellular immunity and the other for forming the antibodies that provide humoral immunity.

Both of these types of lymphocytes are derived originally in the embryo from lymphocytic stem cells in the bone marrow. The descendants of the stem cells eventually migrate to the lymphoid tissue. Before doing so, however, those lymphocytes that are eventually destined to form sensitized lymphocytes first migrate to and are preprocessed in the thymus gland, for which reason they are called "T" lymphocytes. These are responsible for cellular immunity.

The other population of lymphocytes—those that are destined to form antibodies—is processed in some unknown area of the body, possible the liver and spleen. However, this population of cells was first discovered in birds in which the preprocessing occurs in the bursa of Fabricius, a structure not found in mammals. For this reason this population of lymphocytes is called the "B" lymphocytes, and they are primarily responsible for humoral immunity.

To further emphasize that the two populations of lymphocytes are separate, it is known that they also tend to localize in separate parts of the lymphoid tissue. For instance, in the lymph nodes, the lymphocytes of the "B" system are mainly located in the cortical and germinal areas, whereas the "T" cells are located in the paracortical areas.

After formation of processed lymphocytes in the thymus, these first circulate freely in the blood and gradually filter into the tissues. Then they enter the lymph and are carried to the lymphoid tissue. The lymphoid tissue contains reticulum cells that form a fine reticulum meshwork. This filters the lymphocytes from the lymph, thereby entrapping them in the lymphoid tissue. Thus, the lymphocytes do not originate Primordially in the lymphoid tissue, but instead are transported to this tissue by way of the preprocessing areas of the thymus and probably the fetal liver.

When a lymphocyte in the lymphoid tissue is stimulated to form either sensitized lymphocytes or antibodies, it always forms a sensitized lymphocyte or an antibody having specificity for a particular antigen. Because it is known that the lymphocytes of the lymphoid tissue can form literally hundreds or thousands of different types of sensitized lymphocytes and antibodies specific for different antigens, it is also almost certain that literally hundreds or thousands of different types of precursor lymphocytes pre-exist in the lymph nodes for formation of the many specific types of lymphocytes or antibodies.

The lymphocytes of each specific type in the lymphoid tissue—those that form one specific type of sensitized lymphocyte or one specific type of antibody—are called a "clone of lymphocytes."

Each clone of a lymphocyte is responsive to only a single type of antigen (or to a group of antigens that have almost exactly the same stereo-chemical characteristics). When excited by the clone's specific antigen, all the cells of the clone proliferate madly, forming tremendous numbers of progeny, and these in turn lead to the formation of large quantities of antibodies if the clone is "B" lymphocytes, or to the formation of numerous sensitized lymphocytes if the clone is "T" lymphocytes.

On exposure to proper antigens, sensitized lymphocytes are released from lymphoid tissue in ways that parallel antibody release except that instead of releasing antibodies, whole sensitized lymphocytes are formed and released from the lymphoid tissue into the lymph.

An important difference between cellular immunity and humoral immunity is its persistence. Humoral antibodies rarely persist more than a few months, or at most a few years. On the other hand, sensitized lymphocytes probably have an indefinite life span and seem to persist until they eventually come in contact with their specific antigen. There is reason to believe that such sensitized lymphocytes might persist as long as ten years in some instances.

Although the humoral antibody mechanism for immunity is especially efficacious against more acute bacterial diseases, the cellular immunity system is activated much more potently by the more slowly developing bacterial diseases such as tuberculosis, brucellosis, and so forth. Also, this system is active against neoplastic cells, cells of transplanted organs, and fungal organisms, all of which are far larger than bacteria. And, finally, the system is very active against some viruses.

Therefore, cellular immunity is especially important in protecting the body against some viral diseases, in destroying many early cancerous cells before they begin to grow, and, unfortunately, in causing rejection of tissues transplanted from one person to another.

The sensitized lymphocyte, on coming in contact with its specific antigen, combines with the antigen. This combination in turn leads to a sequence of reactions whereby the sensitized lymphocytes destroy the invader. As is also true of the humoral immunity system, the sensitized lymphocyte destroys the invader either directly or indirectly.

Sensitized lymphocytes can become bound with antigens in the membrane of an invading cell such as a cancer cell, a heart transplant cell, or a parasitic cell of another type. The immediate effect of this attachment is swelling of the sensitized lymphocyte and cause immediate release of cytotoxic substances from the lymphocyte to attack the invading cell.

When sensitized lymphocytes combine with their specific antigens, they can release a number of different substances into the surrounding tissues that lead to a sequence of reactions. These reactions in turn are much more potent than the original attack on the invader. These include release of transfer factors which "recruit" additional lymphocytes having the same capability for causing the same cellular immunity reaction as the originally sensitized lymphocytes and includes the attraction and activation of macrophages to enhance their phagocytic and bacteriacidal functions.

It is by a combination of a weak direct effect of the sensitized lymphocytes on the antigen invader and much more powerful indirect reactions that the cellular immunity system destroys the invader.

Obviously, if a person should become immune to his own tissues, the process of acquired immunity would destroy his own body. Fortunately, the immune mechanism normally "recognizes" a person's own tissues as being completely distinctive from those of invaders, and his immunity system forms neither antibodies nor sensitized lymphocytes against his own cells and tissues. This phenomenon is known as tolerance to the body's own tissues.

Several researchers have described direct cell-mediated cytotoxicity against tumors. These include, for example, descriptions of T-cell killing, (Vanky F, Klein E., "Human T-cell cultures with selective antitumor reactivity," Cancer Immunol Immunother 1982;14:73–7; Vose BM, Bonnard GD, "Specific cytotoxicity against autologous tumor and proliferative responses to human lymphocytes grown in interluekin 2." Int. J. Cancer 1982;29L33-9; Wunderlich J., "Short-term $^{51}$Cr-release tests for direct cell-mediated cytotoxicity: methods, clinical uses and interpretations." In: Bach FH, Good RA, eds. Clinical immunobiology. New York: Academic Press, 1976:133–48); killing by macrophages, (Hibbs JB. "The macrophage as a tumoricidal effector cell: a review of in vivo and in vitro studies on the mechanism of the macrophage non-specific cytotoxic reaction." In: Fink MA, ed. The Macrophage In Neoplasia. New York: Academic Press, 1976:83–112); natural cytotoxicity, (Stutman O, Lattime EC. "Natural cell-mediated cytotoxicity against tumors in mice: an heterogeneous system, " Transplant Proc. 1981;13:752-5); polyinosinic acid-induced cytotoxicity, (Dorfman N, Winkler D, Burton RC, Kassayda N, Sabia P, Wunderlich J., " Broadly reactive murine cytotoxic cell induced in vitro under syngeneic conditions," J. Immunol. 1982;129-17-62–9); lectin-induced cytotoxicity, (Mazumder A. Grimm EA, Zhang HZ, Rosenberg SA, "Lysis of fresh human solid tumors by autologous lymphocytes activated in vitro with lectins. Cancer Res. 1982;42:913–8); and interleukin induced cytotoxicity, (Grimm EA, Mazumder A, Zhang HZ, Rosenberg SA, Lymphokine-activated killer cell phenomenon," J. Exp. Mec. 1982;55: 1823–41). Lectin-induced cytotoxicity and interleukin induced cytotoxicity represent polyclonal activation of T-cells.

It is widely known that spontaneously arising tumor cells are usually not sufficiently antigenic to induce an immune response. (Eggers et. al. Cancer Immunol. Immunother. (1982)).

Adjuvant peptides have been used to stimulate the immunogencity of tumors. Adjuvants in general, are substances which non-specifically enhance the immune response to an antigen. It is known that in certain instances, administration of an antigen together with an adjuvant can completely change the mode of response, i.e., it is possible to break self tolerance to a large number of self or syngeneic antigens by injecting them into the host animal in an appropriate adjuvant. The most frequently utilized adjuvants are water-in-oil emulsions with the antigen in the aqueous phase, for example, Freund's Adjuvant. The adjuvant properties can be further enhanced by the addition of microbial antigen to the mixture such as in Freund's complete Adjuvant which contains heat-killed Mycobacterium tuberculosis.

Antibody responses to antigens in adjuvants have proven to be greater, more prolonged and consist of different classes to the response obtained without an adjuvant. Adjuvants are hypothesized to work in a variety of ways. Initially, an antigen in an emulsion is resistant to dispersal and it therefore acts as a reservoir for antigen stimulation for a period of long duration. Moreover, microbial products in general activate macrophages which lead to the Production of antigen non-specific factors which enhance the response. (Ivan M. Roitt et. al. IMMUNOLOGY Gower Medical Publishing, New York 1985).

In order to assist the body's own immune system in combating neoplastic diseases, such as all solid and lymphoid tumors, in vitro and in vivo immunization against tumor cell antigens has been performed.

In contrast to the non T-cell and polyclonal T-cell systems, it has been demonstrated that the use of an adjuvant peptide (AP) such as N-acetyl muramyl-L-alanyl-D-isoglutamine, covalently bound to the surface of poorly antigenic tumor cells such as murine methylcholanthrene-induced sarcoma cells (MC-1 cells) increases tumor immunogencity by permitting the induction of direct cell-mediated cytotoxicity against tumor associated antigens. This immunity is thus antigen driven and T-cell mediated.

The cell mediated cytotoxicity against tumor cells antigens has been shown to also be directed against cross reacting "targets" including many non H-2 (H=histo compatibility) matched solid tumors and some normal cells. This technique has been shown to work in vitro and in vivo, and a therapeutic effect has been demonstrated in vivo with small tumors. (Eggers, et. al. "Use of Covalently Bound Adjuvant Peptide to Increase Tumor Immunogenicity", Cancer Immunol Immunother; 12:167–172, 1982; Eggers, et. al. "T-cell nature of Adjuvant Peptide-Induced Antitumor cell-mediated cytotoxicity", J. Biological Response Modifiers, 3:387–390, 1984, Eggers et. al. "In vivo immunization against autologous glioblastoma-associated antigens, Cancer Immunol. Immunother. 19:43–45 (1985) the disclosures of which are incorporated by reference herein).

It has been demonstrated that experimental animals as well as humans can elicit an immune response against their own neoplastic cells. It has been, therefore, somewhat of an enigma why, when humans are capable of such as immune response, in most cases, the tumor continues to grow and or metastasize and finally kills the host instead of being destroyed by an immune reaction of the host. An explanation for this failure has been attempted by David Ilfeld et. al. "In vivo cytotoxicity and in vivo tumor enhancement induced by mouse spleen cells autosensitized in vitro," Int. J. Cancer 12:213–22, 1973.

Ilfeld et. al. hypothesized that circulating antibodies equipped with immunological specificity against tumor antigens accelerate tumor growth by actually interfering with the directed against tumor-specific antigens may favor the acceptance of an antigenic homograft whereas a strong response could lead to tumor rejection. Ilfeld et. al. studied the immuno-reactivity of C57B2 mouse spleen cells previously sensitized in vivo against syngeneic (self) fibroblasts, which were irradiated prior to sensitization. The sensitized spleen cells were assayed in vitro to test their cytotoxicity against 3LL tumor cells. Further, the sensitized spleen cells were mixed with the tumor cells and injected into syngeneic recipient mice in order to assay, in vivo, the influence on tumor growth. The in vitro assay showed that the sensitized lymphoid cells were cytotoxic against fibroblasts as well as against the tumor cells. However, in vivo experiments established that lymphoid cells sensitized against syngeneic fibroblasts promoted the growth of the 3LL tumor.

A problem with using tumor cells to prepare a vaccine is that most human tumors cannot be grown in tissue culture. For example, most common human tumors, such as colon, breast, non-oat cell of the lung and prostate are difficult to grow in sufficient quantities to prepare enough for a single injection.

It is an objective of the present invention to provide a vaccine composition comprising non-malignant cells, preferably syngeneic, non-malignant cells coupled, to an adjuvant for administration to a vertebrate to induce a cell mediated cytotoxic response which cross reacts with tumor cells so that an anti-tumor immunity is induced in the vertebrate.

It is a second objective of the present invention to provide for a method for inducing anti-tumor immunity by administering non-malignant cells, preferably syngeneic, non-malignant cells coupled to an adjuvant as antigens or immunogens to induce in vivo cytolytic activity, i.e., induce an autoimmune response against the non-malignant cells that cross-reacts against neoplastic or tumor cells and induces in vivo protection against tumor cells.

It is a third objective of the present invention to provide a method for the treatment of neoplastic disease in a vertebrate comprising administering a therapeutically effective amount of non-malignant cells coupled with an adjuvant.

SUMMARY OF THE INVENTION

The present invention relates to the preparation of a vaccine comprising non-malignant cells and preferably syngeneic, non-malignant cells coupled to an adjuvant to sufficiently derivatize the cells such that an immune response is generated.

The present invention further relates to the use of non-malignant cells coupled to an adjuvant to induce anti-tumor immunity and thus Presents a novel method for tumor immunotherapy.

The present invention also relates to a vaccine composition for inducing anti-tumor immunity in a vertebrate comprising a therapeutically effective amount of non-malignant cells coupled with an adjuvant.

It has now been found that the use of non-malignant cells, coupled to adjuvants as immunizing cells, induces T-cell mediated cytotoxicity to the immunizing cells which cross-reacts with tumor cells and particularly with syngeneic tumor cells. Non-malignant or syngeneic cells coupled to an adjuvant become derivatized such that they are rendered immunogeneic. When they are administered to a vertebrate as a vaccine composition, the vertebrate elicits a cell mediated cytolytic immune response against the derivatized cells as well as against tumor cells, due to cross reactivity between the cells.

Thus, for the first time, evidence is presented that non-malignant cells coupled to an adjuvant to derivatize the cells can induce in vitro cytolytic activity and in vivo protection against tumor cells.

DETAILED DESCRIPTION OF THE INVENTION

A vaccine preparation and a method for inducing anti-tumor immunity in vivo is provided.

Non-malignant or non-neoplastic cells and preferably syngeneic non-malignant cells, such as, for example, fibroblasts, kidney fibroblasts, epithelial cell lines and lymphoid cells are mixed in solution with or coupled to, or preferably covalently coupled, to an adjuvant, preferably an adjuvant Peptide, such as, for example, muramyl dipeptide; the p-nitrophenyl ester of muramyl dipeptide (N-acetylmuramyl-L-alanyl-D-isoglutamine), the p-nitrophenyl ester of cord factor analog (trehalosedihemisuccinatemonohexadecylamide) or other adjuvants derived from or synthesized to resemble components of bacterial or fungal cell walls which have a reactive carboxyl, amino, or sulfhydryl group capable of activation for covalent coupling to cells.

The use of the adjuvant derivatizes the non-malignant cells and breaks the vertebrate's tolerance to the non-malignant cells and, therefore, enhances immunogenicity. The sensitized lymphocytes display cross-reactivity against tumor antigens and thus induce anti-tumor immunity.

Optionally, a spacer or bridge is inserted or interposed between the adjuvant and the non-malignant cell surface to further enhance immunogenicity. Examples of suitable spacers or bridges include, glycylglycylcystamide, meta-maleimidobenzoyl-N-hydroxysuccinimide ester, N-succinimidyl-3-(2-pyridyldithio) propionate or other compounds capable of cross-linking proteins.

Suitable adjuvants and/or spacers are known and are prepared-- according to the methods as disclosed in Eggers, et al. "Use of Covalently Bound Adjuvant Peptide to Increase Tumor Immunogenicity", *Cancer Immunol Immunother;* 12:167-172, 1982; Eggers, et. al. "T-cell nature often Adjuvant Peptide-Induced Antitumor cell-mediated cytotoxicity", *J. Biological Response Modifiers,* 3:387-390, 1984, Eggers et. al. "In vivo immunization against autologous glioblastoma-associated antigens, *Cancer Immunol. Immunother.* 19:43-45 (1985) and Eggers et. al. "Use of Covalently Bound Cord Factor Analog to Increase Tumor Immunogenicity", *J. Biological Resp. Modifiers,* 3:413-422 (1984), the disclosures of which are incorporated by reference herein).

The mixture or vaccine composition thus comprises non-malignant cells coupled to adjuvants. The Present composition may be administered in any manner which is traditional for administration of vaccine type compositions, e.g., parenteral, intraperitoneal or subcutaneous injections, and as capsules or tablets for oral administration.

When oral preparations are desired, the compounds may be combined with typical carriers, such as lactose, sucrose, starch, talc magnesium stearate, crystalline cellulose, methyl cellulose, hydroxypropyl cellulose, hyroxypropylmethyl cellulose, carboxymethyl cellulose, glycerin, sodium alginate or gum arabic among others. For parenteral or intraperitoneal administration, suitable carriers such as, for example, water or physiological saline may be employed.

The periodicity of the administration of the composition may be varied in accordance standard practices apparent to the treating physician.

Immunization in vivo against the afore-described non-malignant cells coupled with an adjuvant leads to lymphocytic development of direct cell-mediated cytotoxicity to the immunizing cells. The sensitive lymphocytes cross-react against tumor cells and thus provides in vivo protection against tumor cells.

Examples of tumors capable of being treated by the vaccine composition and method of the present invention include, for example, fibrosarcomas, glioblastomas, and all solid and lymphoid tumors.

In vivo immune activity or auto sensitization to syngeneic non-malignant cells with cross reactivity against tumor cells is, for the first time, detectable by short-term CRA or $^{51}$Chromium Release Assay as described in, for example, Eggers et. al. "In Vitro Immunization Against Autologous Glioblastoma Cells Coupled to Adjuvant Peptide." *J. Neurol. Sci.* 3:387-390 1984; and Eggers et. al. "Chemical Enhancement of Tumor Immunogenicity," *J. Immunol.,* 125:1737 (1980) which are herein incorporated by reference. Although the exact nature of the tumor antigens detected is not fully known, the present invention, for the first time demonstrates a connection between the anti-tumor immunity induced by tumor cells coupled adjuvants against tumor cells on the one hand and autoimmunity to normal or non-malignant cells on the otherhand. Thus, the Present invention may provide clues concerning the nature of certain tumor-associated antigens, the cross-reactivity of non-malignant cells, in particular fibroblasts, and tumor cells and also evidences for the first time that derivatized non-malignant cells function as immunogens and are useful in vivo tumor immunotherapy.

One theory could be that the cross-sensitization of fibroblasts and tumor cells is due to the shared immunity is directed against one or more families of growth factor receptors. Both growth factors and their receptors have been identified as the translational products of oncogenes (Heldin C-H, Westermark B. Growth factors:mechanism of action and relation to oncogenes. *Cell,* 1984; 37:9-20; DeLarco JE, Todaro GJ. Growth factors from murine sarcoma virus-transformed cells. *Proc Nat Acad Sci USA* 1978; 75:4001-5.)

The cytolytic activity, in vivo against tumor cells displayed by organisms treated in accordance with the present invention is intended to be understood as affecting all stages of tumor development. That is to say that the use of non-malignant cells coupled with adjuvants induces sensitized lymphocytes to develop direct cell-mediated cytotoxicity against the non-malignant cells and also to display cross-reactivity against tumor cells and can prevent tumor growth as well as destroy tumor cells.

The vaccine composition may be used in treatment of neoplastic disease including cancer in any vertebrate, in particular, warm-blooded vertebrates, particularly humans.

The present invention may be better understood by reference to the following non-limiting examples which demonstrate the effective use of the present invention.

EXAMPLE 1

PREPARATION OF THE VACCINE COMPOSITION

C57BL/6 (B6) mice were obtained from Charles River Breeding Laboratories (Wilmington, MA) and used at 4-8 weeks of age. A line of B6 kidney fibroblasts (KF) was started by mincing, with forceps, the kidney of a 4 week old mouse and waiting several weeks for an explant line to grow. KF cells were maintained in Eagle's minimum essential medium with 10% fetal calf serum (FCS) (GIBCO, Grand Island, NY). MC-1 cells, a B6 methylcholanthrene-induced fibrosarcoma, were passaged in the same medium with 10% horse serum (GIBCO) as were EL4 cells, a B6 lymphoma. KF cells were used on the third to sixth passages, MC-1 cells on the 75th-78th passages. Spleen cells were stimulated in a 5-day in vitro culture containing 15% FCS. Antigen cells were inactivated with mitomycin-C and bound to muramyl dipeptide (MDP) through a glycylglycylcystamide spacer. Half of the cells were bound to the spacer at a concentration of 2.0 mM and the other half at 0.5 mM. The cells were then pooled and reacted with the p-nitrophenyl ester of MDP, half at a concentration of $10^{-4}$ mM and another half at $10^{-6}$ mM. The cells were then again pooled and used at antigen doses of $10^3$, $10^4$ and $10^5$ MC-1 cells per well in an in vitro immunization procedure.

EXAMPLE 2

In Vitro Immunization

Lymphocytes from wells with different antigen doses were pooled when harvested on day 5 for use in the short-term $^{51}$Cr-release assay (CRA). Direct cell-mediated cytotoxicity is measured with this assay. The CRA was run for 6 hrs with an attacker/target ratio of 200:1. Medium controls i.e. cells incubated in medium in the CRA averaged 10–15%. The percent cell lysis seen with attackers cultured without stimulating cells ("background lysis"), which averaged 0–5% above medium control, was substracted from Percent absolute lysis to give percent specific lysis, and is referred to in Table 1 as "% lysis".

When studied with regard to the development of cytotoxicity, both KF cells and MC-1 cells could function as targets and, if derivatized, as immunogens as well (Table 1). There was cross-reactivity between the two cell types at both the sensitization and target cells stages: that is, each cell type induced cytotoxicity both against itself and against the other cell type.

EXAMPLE 3

In Vivo Protection Challenge

In the protection- challenge experiment, as shown in Table 2 immunogen cells were treated with mitomycin, spacer, and MDP in the same way as for in vitro immunization.

In the in vivo protection-challenge experiment, KF cells were rendered immunogeneic by coupling to adjuvant (Table 2). MC-1 cells were protective even without derivatization. MC-1 cells appeared to be "better" antigens than KF cells in that plain MC-1 cells were protective at all doses of tumor challenge, whereas plain KF cells were protective only against the lowest ($10^3$) challenge dose.

Derivatized fibroblasts and derivatized MC-1 cells were equally effective.

TABLE 1

Cross-Reactivity of Syngeneic Kidney Fibroblasts and MC-1 tumor cells[a]

| Immunogen | % lysis + SE | |
|---|---|---|
| | plain MC-1 | plain KF |
| plain MC-1 | 0.2 ± 0.3 | 1.0 ± 0.9 |
| MC1-MDP | 38.2 ± 3.1 | 29.0 ± 1.2 |
| plain KF | 0.8 ± 1.0 | 0.7 ± 0.5 |

TABLE 1-continued

Cross-Reactivity of Syngeneic Kidney Fibroblasts and MC-1 tumor cells[a]

| Immunogen | % lysis + SE | |
|---|---|---|
| | plain MC-1 | plain KF |
| KF-MDP | 28.5 ± 2.3 | 25.4 ± 1.8 |

[a]Splenocytes were immunized in vitro against MC-1 and KF cells either left unmodified or coupled to spacer and MDP (muramyl dipeptide). Effectors were harvested after 5 days and run in a short-term CRA against unmodified MC-1 or KF targets.

TABLE 2

Effectiveness of Kidney Fibroblasts in A Protection-Challenge Experiment[a]

| | No. of mice with growth of MC-1 challenge tumor Dose of challenge tumor | | |
|---|---|---|---|
| Immunogen | $10^3$ | $10^4$ | $10^5$ |
| None | 3/3 | NT | NT |
| EL4-MDP | 4/5 | 5/5 | 5/5 |
| plain MC-1 | 0/5 | 0/5 | 0/5 |
| MC-1-MDP | 0/5 | 0/5 | 0/5 |
| plain KF | 1/5 | 5/5 | 5/5 |
| KF-MDP | 0/5 | 0/5 | 0/5 |

[a]Mice were injected intraperitoneally, (IP) with two doses two weeks apart of $10^6$ immunogen cells treated as indicated. One week later they were challenged with untreated MC-1 cells injected subcutaneously in the left flank. Animals were followed four weeks for tumor outgrowth. NT = not tested.

What is claimed is:

1. A vaccine composition for inducing immunity in a mammal against a tumor selected from the group consisting of sarcomas, gliomas, and carcinomas, comprising a therapeutically effective amount of non-malignant mammalian fibroblast cells covalently coupled with an adjuvant in a pharmaceutically acceptable medium, said adjuvant selected from the group consisting of muramyl dipeptide, the p-nitrophenyl ester of muramyl dipeptide (N-acetylmuramyl-L-alanyl-D-isoglutamine), the p-nitrophenyl ester of cord factor analog, and other adjuvants derived from or synthesized to resemble components of bacterial or fungal cell walls which have a reactive carboxyl, amino, or sulfhydryl group capable of activation for vonalent coupling to cells.

2. A vaccine composition according to claim 1 wherein the non-malignant cells are syngeneic cells.

3. A vaccine composition according to claim 1 or claim 2 wherein the tumor is selected from the group consisting of fibrosarcoma and glioblastoma.

4. A vaccine composition according to claim 1 wherein the adjuvant is selected from the group consisting of muramyl dipeptide, the p-nitrophenyl ester of muramyl dipeptide (N-acetylmyramyl-L-alanyl-D-isoglutamine) and the p-nitrophenyl ester of cord factor analog.

5. A vaccine composition according to claim 1 or 4 wherein a spacer is interposed between the non-malignant cell surface and the adjuvant.

6. A vaccine composition according to claim 5 wherein the spacer is a glycylglycylcystamide spacer.

7. A vaccine composition according to claim 1 wherein the mammal is a mouse and the non-malignant cells are mouse fibroblasts.

8. A vaccine composition according to claim 1 wherein the mammal is a human and the non-malignant cells are human fibroblasts.

9. A vaccine composition according to claim 2 wherein the mammal is a human and the non-malignant cells are human fibroblasts.

10. A vaccine composition according to claim 3 wherein the mammal is a human and the non-malignant cells are human fibroblasts.

11. A vaccine composition according to claim 4 wherein the mammal is a human and the non-malignant cells are human fibroblasts.

12. A vaccine composition according to claim 5 wherein the mammal is a human and the non-malignant cells are human fibroblasts.

13. A vaccine composition according to claim 6 wherein the mammal is a human and the non-malignant cells are human fibroblasts.

14. A method for inducing immunity against a tumor selected from the group consisting of sarcomas, gliomas, and carcinomas, in a mammal which comprises administering to the mammal a therapeutically effective amount of a vaccine composition comprising nonmalignant mammalian fibroblast cells covalently coupled with an adjuvant selected from the group consisting of muramyl dipeptide, the p-nitrophenyl ester of muramyl dipeptide (N-acetylmuramyl-L-alanyl-D-isoglutamine), the p-nitrophenyl ester of cord factor analog, or other adjuvants derived from or synthesized to resemble components of bacterial or fungal cell walls which have a reactive carboxyl, amino, or sulfhydryl group capable of activation for covalent coupling to cells.

15. A method according to claim 14 wherein the non-malignant cells are syngeneic cells.

16. A method according to claim 14 or 15 wherein the tumor is selected from the group consisting of fibrosarcoma and filoblastoma.

17. A method according to claim 14 wherein the adjuvant is selected from the group consisting of muramyl dipeptide, the p-nitrophenyl ester of muramyl dipeptide (N-acetylmuramyl-L-alanyl-D-isoglutamine) and the p-nitrophenyl ester of cord factor analog.

18. A method according to claim 14 or 17 wherein a spacer is interposed between the non-malignant cell surface and the adjuvant.

19. A method according to claim 18 wherein the spacer is a glycylglycylcystamide spacer.

20. A method according to claim 14 wherein the mammal is a mouse and the non-malignant cells are mouse fibroblasts.

21. A method according to claim 14 wherein the mammal is a mouse and the non-malignant cells are mouse fibroblasts.

22. A method according to clam 15 wherein the mammal is a human and the non-malignant cells are human fibroblasts.

23. A method according to claim 16 wherein the mammal is a human and the non-malignant cells are human fibroblasts.

24. A method according to claim 17 wherein the mammal is a human and the non-malignant cells are human fibroblasts.

25. A method according to claim 18 wherein the mammal is a human and the non-malignant cells are human fibroblasts.

26. A method according to claim 19 wherein the mammal is a human and the non-malignant cells are human fibroblasts.

* * * * *

UNITED STATES PATENT AND TRADEMARK OFFICE
CERTIFICATE OF CORRECTION

PATENT NO. : 5,208,022
DATED : May 4, 1993
INVENTOR(S) : Arnold E. Eggers

It is certified that error appears in the above-indentified patent and that said Letters Patent is hereby corrected as shown below:

In the Abstract, line 7, delete "turmors" and insert --tumors--.

column 1, line 18, delete "posses" and insert --possesses--.

column 1, line 31, delete "Phagocytosis" and insert --phagocytosis--.

column 1, line 47, delete "Protection" and insert --protection--.

column 1, line 53, delete "Particular" and insert --particular--.

column 2, line 32, delete "possible" and insert --possibly--.

column 2, lines 53-54, delete "Primordially" and insert --primordially--.

column 3, line 12, delete " "B" lymphocytes" and insert --a "B" lymphocyte--.

column 3, lines 13-14, delete " "T" lymphocytes" and insert --a "T" lymphocyte--.

column 3, line 55, delete "cause".

column 3, line 68, delete "bacteriacidal" and insert --bactericidal--.

column 4, line 22, delete "1982; 29L33-9" and insert --1982; 29:33-9--.

column 4, line 26, delete "JB." and insert --JB,--.

column 4, line 32, delete "EC." and insert --EC,--.

column 4, lines 38-39, delete "129-17-62-9" and insert --129:1762-9--.

column 4, line 45, insert --"--between"," and "Lymphokine-".

UNITED STATES PATENT AND TRADEMARK OFFICE
CERTIFICATE OF CORRECTION

PATENT NO. : 5,208,022

DATED : May 4, 1993

INVENTOR(S) : Arnold E. Eggers

Page 2 of 5

It is certified that error appears in the above-indentified patent and that said Letters Patent is hereby corrected as shown below:

column 4, line 67, delete "complete" and insert --Complete--.

column 5, line 7, delete "for-a" and insert --for a--.

column 5, line 9, delete "Production" and insert --production--.

column 5, line 27, delete "cells" and insert --cell--.

column 5, line 36, after "Immunother" delete ";" and insert --.--.

column 5, lines 36-38, delete "T-cell nature of Adjuvant Peptide-Induced Antitumor cell-mediated cytotoxicity" and insert --T-Cell Nature of Adjuvant Peptide-Induced Antitumor Cell-Mediated Cytotoxicity--.

column 5, line 38, delete "," after "Modifiers".

column 5, line 39, after "1984", delete "," and insert --;--.

column 5, line 40, insert -- "-- after "antigens,".

column 5, line 41, delete "Cancer Immunol. Immunother. 19:43-45 (1985) and insert --Cancer Immunol. Immunother. 19:43-45, 1985;--.

column 5, line 48, delete "as" and insert --an--.

column 5, line 52, after "et al." insert --in--.

column 5, line 59, after "the" and before "directed", insert --cell mediated response. Therefore, a weak immune response--.

UNITED STATES PATENT AND TRADEMARK OFFICE
CERTIFICATE OF CORRECTION

PATENT NO. : 5,208,022
DATED : May 4, 1993
INVENTOR(S) : Arnold E. Eggers

It is certified that error appears in the above-indentified patent and that said Letters Patent is hereby corrected as shown below:

column 6, line 17, delete "cells coupled," and insert --cells, coupled--.

column 6, line 25, delete "cells coupled" and insert --cells, coupled--.

column 6, line 46, delete "Presents" and insert --presents--.

column 6, line 51, delete "hon-malignant" and insert --non-malignant--.

column 7, line 10, delete "coupled, to" and insert --coupled to,--.

column 7, line 11, delete "Peptide" and insert --peptide--.

column 7, line 18, delete "cr" and insert --or--.

column 7, line 34, delete "prepared--" and insert --prepared--.

column 7, line 37, delete "Immunol Immunother;" and insert --Immunol. Immunother.--.

column 7, lines 38-39, delete "T-cell nature often Adjuvant Peptide-Induced Antitumor cell-mediated cytotoxicity" and insert --T-Cell Nature of Adjuvant Peptide-Induced Antitumor Cell-Mediated Cytotoxicity--.

column 7, line 40, after "1984", delete "," and insert --;--.

column 7, line 42, delete "antigens," and insert --antigens",--.

column 7, line 43, delete "(1985)" and insert --, 1985;--.

column 7, line 45, delete "(1984)" and insert --, 1984--.

UNITED STATES PATENT AND TRADEMARK OFFICE
CERTIFICATE OF CORRECTION

PATENT NO. : 5,208,022
DATED : May 4, 1993
INVENTOR(S) : Arnold E. Eggers

It is certified that error appears in the above-indentified patent and that said Letters Patent is hereby corrected as shown below:

column 7, line 49, delete "Present" and insert --present--.

column 7, line 65, insert --with-- between "accordance" and "standard".

column 8, line 9, delete "auto sensitization" and insert --auto-sensitization--.

column 8, line 15, delete "Peptide." and insert --Peptide,--.

column 8, line 20, insert --,-- between "time" and "demonstrates".

column 8, line 22, insert --to-- between "coupled" and "adjuvants".

column 8, line 24, delete "otherhand" and insert --other hand--.

column 8, line 24, delete "Present" and insert --present--.

column 8, line 36, delete "B. Growth" and insert --B, "Growth--.

column 8, line 37, delete "oncogenes." and insert --oncogenes,"--.

column 8, line 38, delete "Cell," and insert --Cell--.

column 8, line 38 delete "GJ. Growth" and insert --GJ, "Growth--.

column 8, line 39, delete "." and insert --,--.

column 8, line 41, delete "cytolytic activity, in vivo" and insert --in vivo cytolytic activity--.

column 8, line 53, delete "particular," and insert --particular--.

column 9, line 28, insert --,-- after "controls" and before "i.e.".

UNITED STATES PATENT AND TRADEMARK OFFICE
CERTIFICATE OF CORRECTION

PATENT NO. : 5,208,022
DATED : May 4, 1993
INVENTOR(S) : Arnold E. Eggers

It is certified that error appears in the above-indentified patent and that said Letters Patent is hereby corrected as shown below:

column 9, line 28, insert --,-- after "medium" and before "in".

column 9, line 32, delete "Percent" and insert --percent--.

column 9, line 47, insert --,-- between "Table 2" and "immunogen".

In Claim 1, column 10, line 42, delete "vonalent" and insert --covalent--.

In Claim 4, column 10, line 51, delete "acetylmyramyl" and insert --acetylmuramyl--.

In Claim 14, column 11, line 22, delete "or" and insert --and--.

In Claim 16, column 11, line 32, delete "filoblastoma" and insert --glioblastoma--.

In Claim 21, column 12, lines 15 and 16, delete "mouse" and insert --human--.

Signed and Sealed this

Thirty-first Day of May, 1994

*Attest:*

BRUCE LEHMAN

*Attesting Officer*    *Commissioner of Patents and Trademarks*